United States Patent
Mosaddegh

(10) Patent No.: US 12,419,803 B2
(45) Date of Patent: *Sep. 23, 2025

(54) MEIBOMIAN GLAND ROLLER

(71) Applicant: Lillie A. Mosaddegh, San Francisco, CA (US)

(72) Inventor: Lillie A. Mosaddegh, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/234,976

(22) Filed: Aug. 17, 2023

(65) Prior Publication Data

US 2023/0390146 A1    Dec. 7, 2023

Related U.S. Application Data

(63) Continuation of application No. 18/152,744, filed on Jan. 10, 2023, which is a continuation-in-part of
(Continued)

(51) Int. Cl.
*A61H 15/02* (2006.01)
*A61F 7/00* (2006.01)
*A61H 15/00* (2006.01)

(52) U.S. Cl.
CPC ............ *A61H 15/02* (2013.01); *A61F 7/007* (2013.01); *A61H 15/0092* (2013.01);
(Continued)

(58) Field of Classification Search
CPC .. A61H 7/00; A61H 7/001–005; A61H 7/007; A61H 15/00–02;
(Continued)

(56) References Cited

U.S. PATENT DOCUMENTS 1,710,051 A  *  4/1929  Giacopazzi  ........ A61H 15/0085
601/123
3,699,952 A     10/1972  Waters et al.
(Continued)

OTHER PUBLICATIONS

Blackie, et al., "Treatment for meibomian gland dysfunction and dry eye symptoms with a single-dose vectored thermal pulsation: a review," Current Opinions in Ophthalmology 26(4): pp. 306-313 (Jul. 2015).

(Continued)

*Primary Examiner* — Rachel T Sippel
(74) *Attorney, Agent, or Firm* — Sage Patent Group

(57) ABSTRACT

An eye treatment system can comprise a roller with a handle, a power source, control circuitry coupled to the power source, an axle, coupled to the handle, a heating element within the roller, a cylinder configured to rotate about the axle, a temperature sensor adjacent to a surface of the cylinder, with the temperature sensor spaced apart from the heating element, and one or more arms of the roller that couple a first end of the handle to the axle, wherein at least one of the one or more arms houses first wiring through which power is supplied from the power source to the heating element and houses second wiring connecting the temperature sensor to the control circuitry. The treatment system might also comprise an eye pad comprising a heat-retaining material and sized to be applied to an eyelid of a user when warmed. The eye pad could be gel-filled.

20 Claims, 3 Drawing Sheets

Related U.S. Application Data application No. 17/461,796, filed on Aug. 30, 2021, now Pat. No. 11,571,356, which is a continuation of application No. 15/143,348, filed on Apr. 29, 2016, now Pat. No. 11,103,417.

(60) Provisional application No. 62/155,174, filed on Apr. 30, 2015.

(52) U.S. Cl.
CPC ............... *A61F 2007/0004* (2013.01); *A61F 2007/0078* (2013.01); *A61F 2007/0087* (2013.01); *A61F 2007/0095* (2013.01); *A61H 2015/0014* (2013.01); *A61H 2201/0207* (2013.01); *A61H 2201/0221* (2013.01); *A61H 2201/0228* (2013.01); *A61H 2201/0257* (2013.01); *A61H 2201/10* (2013.01); *A61H 2201/5082* (2013.01); *A61H 2205/024* (2013.01)

(58) Field of Classification Search
CPC ........................ A61H 2201/02–0207; A61H 2201/0221–0235; A61H 2201/1671; A61H 2201/1688; A61H 2201/5082; A61H 2201/5097; A61H 2205/024; A61H 2230/50–505; A61F 2007/0004; A61F 2007/0078; A61F 2007/0087; A61F 2007/0095; A61F 2007/0219; A61F 2007/0241; A61F 9/00718; A61F 7/007
See application file for complete search history.

(56) References Cited

U.S. PATENT DOCUMENTS

| | | | | |
|---|---|---|---|---|
| 5,979,006 A | * | 11/1999 | Stokes | A61H 11/00 D28/7 |
| 6,648,904 B2 | * | 11/2003 | Altshuler | A61F 7/02 492/46 |
| 9,216,028 B2 | * | 12/2015 | Korb | A61F 9/00772 |
| 9,314,369 B2 | * | 4/2016 | Grenon | A61H 7/00 |
| 9,719,977 B2 | | 8/2017 | Korb et al. | |
| 2002/0008101 A1 | * | 1/2002 | Hauschulz | G05D 23/1934 219/535 |
| 2008/0236575 A1 | * | 10/2008 | Chuda | A61B 1/00052 128/200.26 |
| 2013/0048011 A1 | | 2/2013 | Bickford et al. | |
| 2013/0172829 A1 | * | 7/2013 | Badawi | A61F 7/02 604/294 |
| 2013/0197405 A1 | * | 8/2013 | Williams, III | A61F 7/02 601/19 |
| 2013/0288859 A1 | | 10/2013 | Watterson | |
| 2014/0277303 A1 | * | 9/2014 | Biser | A61F 7/02 607/104 |
| 2015/0142087 A1 | * | 5/2015 | Jurna | A61F 7/007 607/99 |
| 2015/0157112 A1 | * | 6/2015 | Daibes | A45D 1/16 132/229 |
| 2015/0165231 A1 | * | 6/2015 | Scheja | A61M 37/00 604/20 |
| 2015/0165238 A1 | * | 6/2015 | Slayton | A61N 7/00 601/2 |
| 2015/0182415 A1 | | 7/2015 | Olkowski et al. | |
| 2015/0320590 A1 | * | 11/2015 | Whitehurst | A61F 7/08 607/109 |
| 2016/0184162 A1 | * | 6/2016 | Grez | A46B 15/0028 601/18 |

OTHER PUBLICATIONS

Qiao, et al., "Emerging treatment options for meibomian gland dysfunction," Clinical Ophthalmology 2013(7): pp. 1797-1803 (Sep. 7, 2013).

* cited by examiner

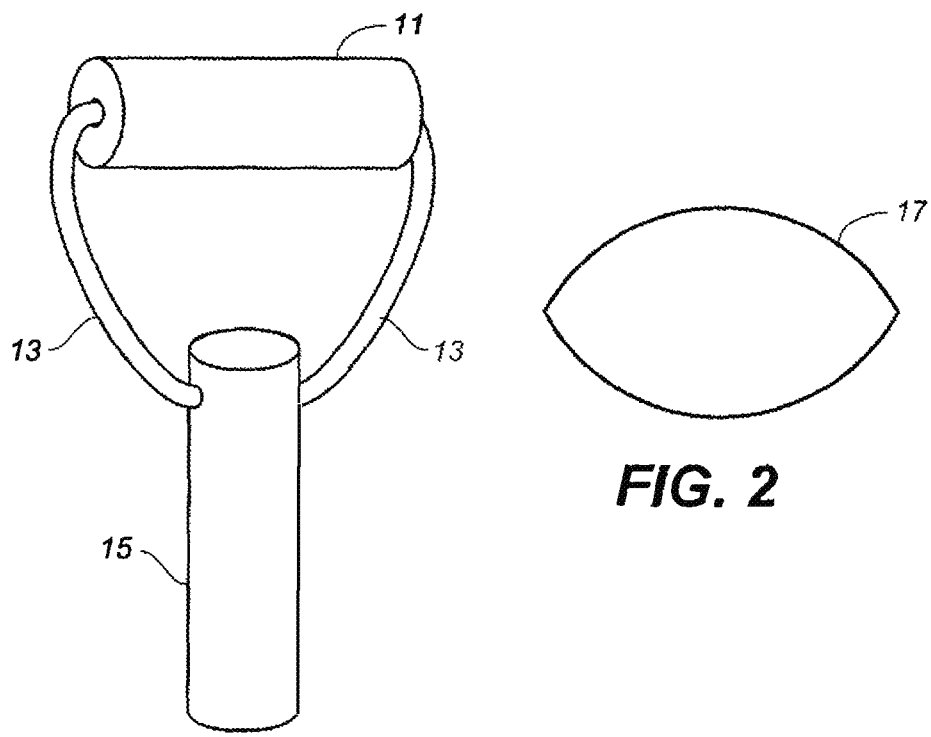
FIG. 1
FIG. 2
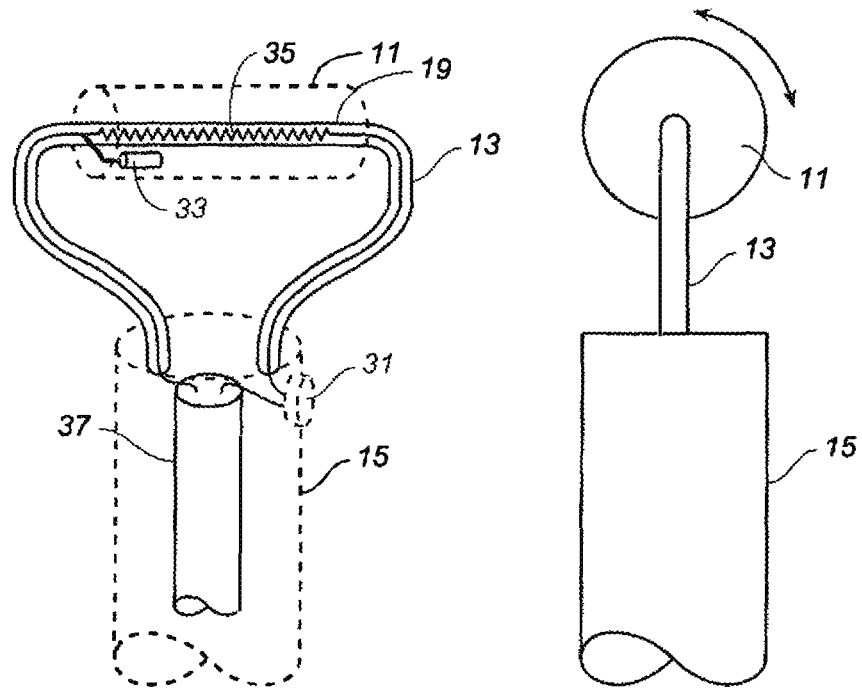
FIG. 3
FIG. 4

MEIBOMIAN GLAND ROLLER

CROSS-REFERENCE TO RELATED APPLICATIONS

This application is a continuation of U.S. patent application Ser. No. 18/152,744 filed on Jan. 10, 2023, which is a continuation-in-part of U.S. patent application Ser. No. 17/461,796, filed Aug. 30, 2021 (now U.S. Pat. No. 11,571,356 issued Feb. 7, 2023, which is a continuation of U.S. patent application Ser. No. 15/143,348, filed on Apr. 29, 2016 (now U.S. Pat. No. 11,103,417 issued Aug. 31, 2021), which claims the benefit of U.S. Provisional Application No. 62/155,174, filed on Apr. 30, 2015.

The entire disclosures of applications/patents recited above are hereby incorporated by reference, as if set forth in full in this document, for all purposes.

FIELD

The present disclosure generally relates to methods and apparatus for treatment of dry eyes and, more specifically, to meibomian gland treatment including the use of eye pads.

BACKGROUND

The meibomian glands (or tarsal glands) are a type of sebaceous gland inside the substance of the eyelids responsible for the supply of meibum, an oily substance that prevents evaporation of the eye's tear film. Meibum prevents tear spillage onto the cheek, trapping tears between the oiled edge and the eyeball, and makes the closed eyelids airtight. Dysfunctional meibomian glands often cause dry eyes, one of the more common eye conditions. Inflammation of the meibomian glands causes the glands to be obstructed by thick waxy secretions. Besides leading to dry eyes, the obstructions can result in other medical problems. Treatment can include expression of the gland by a professional. In some cases, antibiotics or steroids are prescribed.

SUMMARY

A roller includes a cylinder, an axle about which the cylinder can rotate, a handle, and arms. The cylinder and axle include a heating element, and the cylinder is configured to roll over and apply pressure to the eyelid of a user. The handle includes a power source and the axle is held to the handle by the arms and power is supplied by the arms from the power source to the heating element. An eye pad might be included to be placed over the user's eyelid prior to application of the roller.

A method includes warming the cylinder of a roller, where the roller has a handle and arms by which the cylinder is attached to the handle. A user applies pressure to an eyelid of the user by the warmed cylinder and rolls the warmed roller across the user's eyelid to express the meibomian glands.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of methods and apparatus, as defined in the claims, is provided in the following written description of various embodiments of the disclosure and illustrated in the accompanying drawings.

BRIEF DESCRIPTION OF THE DRAWINGS

Various embodiments in accordance with the present disclosure will be described with reference to the drawings, in which:

FIG. 1 illustrates an embodiment of a meibomian gland roller.

FIG. 2 shows an example of an eye pad.

FIG. 3 includes some of the internal detail for the roller structure.

FIG. 4 is a side view of an embodiment of a meibomian gland roller.

DETAILED DESCRIPTION

Figure 5:
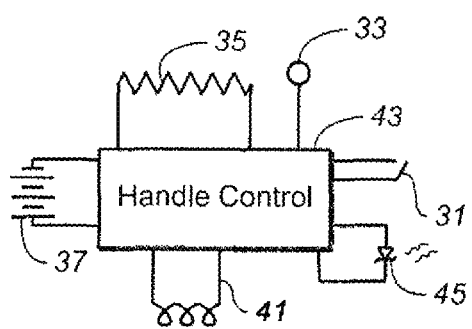
FIG. 5 is a schematic diagram of some electrical elements for an exemplary embodiment of the roller.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

The Meibomian Gland Roller described here is a practical way to self-administer the treatment for one of the leading causes of dry eyes, namely, tear film oil deficiency. This roller combines an effective and safe method to use mechanical rolling pressure combined with heat for meibomian gland drainage. The roller can be distributed as a kit that is a complete package to melt, effectively and safely milk, and wash away the common hardened contents of a dysfunctional meibomian gland.

The device is designed with an externally applied roller that can be applied to a closed eye that can be safely used by the consumer on their own eyelids without the need for a clinician inserting anything into the eye. Additionally, this roller can have an embedded sensor in the roller to control and maintain the temperature at the range of 42 to 45 degrees Celsius. Since eye shape and size vary from person to person, the roller head width will be designed to be about ⅓ of the width of the average adult person's eyelid size, on the order of 1-2 cm, for example. With this size roller, the device can be used on the eyelid of different size adult eyes, as well as the pediatric population.

The rolling action of this instrument, combined with the rolling head increases its effectiveness in emptying inspissated meibomian glands. The roller tip allows the patient to safely start the application of the pressure at the bottom of the glands and effectively roll open the clogged-up oil glands, analogous to squeezing out the contents of a tooth paste tube. The washable roller keeps the head clean for long term use. The removable roller head allows for a multi-user application.

A preheated, eye-shaped, soft eye pad can be used to prepare the eyelids by softening the meibomian gland contents and making it easier for the roller to have a more effective action to induce mechanical extraction of the gland content. As discussed below, a charging well structure can include a well for heating an eye-shaped pad. This allows for eye pads to be heated without use of a microwave to heat the eye pad, which makes it safer as well as more convenient to use. It is safer because no microwaves are used to heat up the eye pad before its application so close to the eye. It can be more convenient since it can be used at any location simply by plugging it into an electric outlet or using the rechargeable battery. The eye pad can be designed to maintain the temperature between 42 and 45 degrees Celsius for 3 to 5 minutes or longer.

In some configurations and treatment processes, the eye pad is applied to the user's eyelid and is in place while the roller is applied. In some embodiments, the eye pad comprises a soft gel component, wherein the eye pad comprises an outer surface material enclosing a soft gel. The eye pad could be flat and thin, such as a single or a few layers of fabric or similar thicknesses, or might enclose a gel or silicone capable of absorbing and releasing heat. The eye pad could comprise a gel, silicone, fabric, plastic, or other appropriate material that can provide for the desired heat conduction. An adhesive material can be applied to the eye pad to allow the eye pad to adhere to the user's face around the user's eyelids. In some embodiments, the eye pad is eye-shaped whereas in other embodiments, it has another shape.

In some embodiments, treatment involves pre-heating the eye pad, but in other embodiments the eye pad is not pre-heated prior to application. Some variations of the eye pad could include pressure sensors and/or temperature sensors.

In one set of exemplary embodiments, the components of a roller system can include a heatable roller, having a roller cylinder and handle, an eye pad, a charging base with a well for charging the roller, and a heating well for the eye pad.

FIG. 1 is a schematic element of the roller and eye pad. The roller includes a handle 15, arms 13, and a roller cylinder 11 supported on an axle (not visible in FIG. 1) held by the arms. The arms 13 hold the axle for the roller cylinder and attach to the handle 15, providing electric connections between the handle 15 and the axle and cylinder. The roller cylinder is the part that touches the eyelid. In a first exemplary embodiment, the roller cylinder is of a metal substance and attached to a chargeable handle to keep the roller at the temperature that corresponds to the melting point of the meibum and that is a safe temperature for the skin, such as 42 to 45 degrees Celsius, during application period. Electric power supplied can be supplied to a heating element in the roller by a battery in the handle to maintain this temperature range. The roller materials are preferably washable and comfortable against the skin. The roller can be packaged with additional rollers for future replacement. Also, replacement roller heads can optionally be bought or supplied.

The roller cylinder can include the heating element and a temperature sensor to detect the temperature of the roller. Depending on the embodiment, the heating element can be part of the axle, part of the roller cylinder, or part of the surface of the roller cylinder or just below the surface of the roller cylinder. The temperature sensor, which, depending on the embodiment, is optional, can be located just below the surface of the roller cylinder or part of the axle, for example. The roller cylinder width will be designed to be about ⅓ of the width of the average adult person's eyelid size, on the order of 1-2 cm, for example.

The roller cylinder 11 can be made from metal with an appropriate thermal conductivity, silicone cast resin, or other materials, such as one or more of Teflon™ material, acrylic, bitumen, cellulose acetate, molded material, sheet material, granite, dry leather, limestone, polycarbonate, polymethylmethacrylate, porcelain, polyvinylchloride (PVC), quartz mineral, silicone cast resin, or vinyl ester, or similar materials.

A chargeable handle 15 for the roller can include a rechargeable battery, indicator light, and a switch that is controlled through a control button, as well as a connector to a well for charging the rechargeable battery. Alternately, wireless charging can be used.

FIG. 2 illustrates and example of an eye pad 17, which in this example is more or less eye-shaped. In some configurations and treatment processes, the eye pad is applied to the user's eyelid and is in place while the roller is applied.

In some embodiments, the eye pad comprises a soft gel component. The eye pad could be flat and thin, such as a single or a few layers of fabric or similar thicknesses, or might enclose a gel or silicone capable of absorbing and releasing heat. The eye pad could comprise a gel, silicone, fabric, plastic, or other appropriate material that can provide for the desired heat conduction. An adhesive material can be applied to the eye pad to allow the eye pad to adhere to the user's face around the user's eyelids. In some embodiments, the eye pad is eye-shaped whereas in other embodiments, it has another shape. For example, the eye pad might be an eye-shaped soft gel eye pad. The eye pad could be a heated eye pad.

In some embodiments, treatment involves pre-heating the eye pad, but in other embodiments the eye pad is not pre-heated prior to application. Some variations of the eye pad could include pressure sensors and/or temperature sensors. An eye pad temperature sensor and/or an eye pad pressure sensor could be embedded within the eye pad and possibly able to communicate signals to a device or app for monitoring, displaying, and/or alerting the user to certain alarm or other conditions.

FIG. 3 illustrates an alternative example of an eye treatment roller, with some of the detail internal to both the roller 11 and handle 15 shown inside. The battery is shown at 37, where the wiring then runs through the arms 13 to the axle 19. Here the heating coil 35 is shown to be within the axle 19 and a temperature sensor circuit 33 is in the roller. A control button is represented on the handle at 31.

When the control button 31 is pressed, the switch can connect the rechargeable battery 37 to the heating element 35 and the temperature sensor 33 in the roller cylinder, and to the indicator light in the handle, to supply power to these three devices. When the roller is heated to the desired temperature, this is sensed by the temperature sensor, which can send a signal to the indicator light in the handle and to the charging base to so indicate. When the control button 31 is pressed again, the switch toggles and turns off the connection between the rechargeable battery and the heating element, the temperature sensor in the roller, and the indicator light in the handle.

FIG. 4 is a side view corresponding to FIG. 1.

FIG. 5 is a schematic diagram of some electrical elements for an exemplary embodiment of the roller. The heating coil 35 and temperature sensor 33 are connected through the wiring in the arms to the handle's control circuitry 43. Depending on the embodiment, the rechargeable battery 37 can be charged through a connector or by way of an induction coil 41 for wireless charging. A LED 45 is included for an indicator light on the handle.

Figure 6:
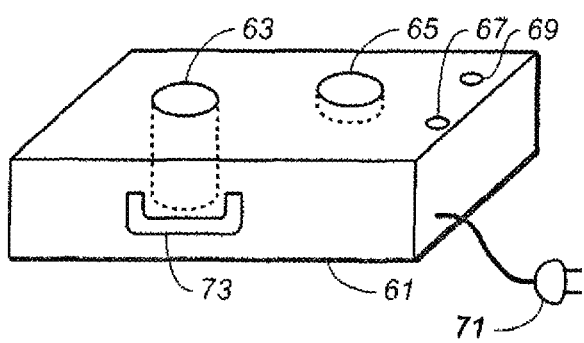
FIG. 6 shows an example of a charging well for the roller system.

FIG. 6 is a view for one embodiment of a charging base 61 with a roller well 63 and a heating well 65 for heating the eye pad, where an additional well can be included for an extra eye pad. The charging well 63 can include a socket for charging the handle, or an induction coil 73 for wireless charging. A cord 71 for connection to a power source. The charging well might receive a second end of the handle that is opposite a length of the handle from the first end. The charging base can also include a built-in rechargeable battery. In this way, it can be used by simply plugging the cord 71 into an electric outlet, as well as using its rechargeable battery to operate it where there is no electricity available. The charging well can be equipped with an on-off switch (not shown) and an indicator light to signal when the arm and the eye pad are at the right temperature to be used.

The eye pad well 65 can heat the eye pad to the appropriate temperature. This allows the eye pad to be heated without use of a microwave oven, for example, as some people prefer not to heat using a microwave oven or it is not nearby to where the device is used. A flexible soft gel eye-shaped pad enclosing gel can be heated to 42-45 degrees Celsius before it is applied to the eyelids. A pair of indicator lights 67 and 69 can indicate the charge state or temperature for the handle and the temperature for eye pad.

Figure 7:
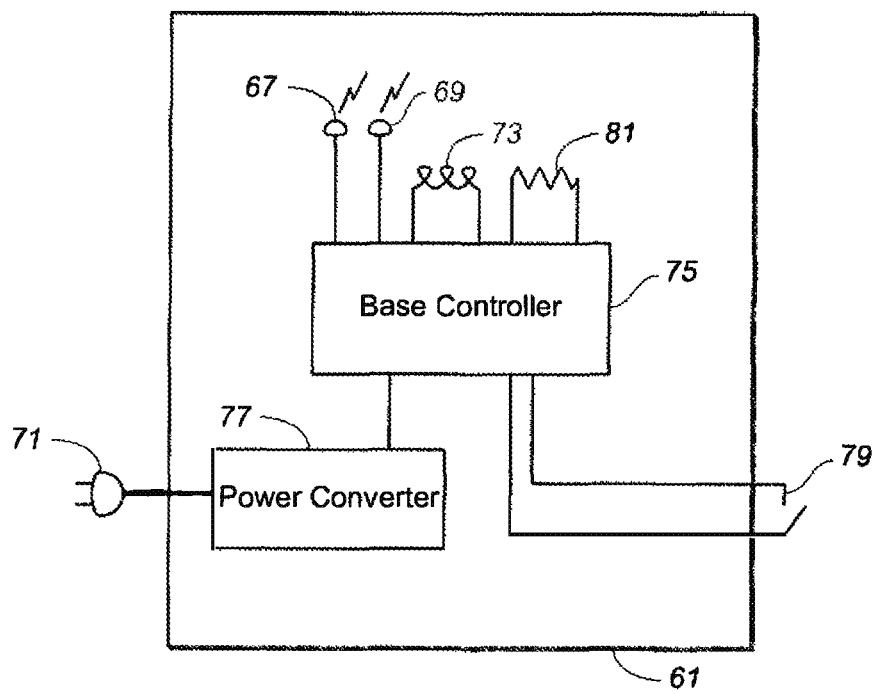
FIG. 7 is a schematic for some elements that can be in the base.

FIG. 7 is a schematic for some elements that can be in the base 61. A base controller 75 can be connected the lights 67 and 69 and induction coil 73, as well as a heating coil 81 for the eye pad. The cord 71 is connected to the power converter 77 that supplies power to the base, and an on-off switch is represented at 79.

The roller can also be used with sweeping applicators, which can be included in a kit with the roller and base, or obtained separately. The sweeping applicators can be individually foil-wrapped double ended sweepers with a presoaked gauze tip. The tips can be presoaked with a mild detergent and anti-bacterial solution.

In a typical application of the roller system, the charging base would be plugged in (or already plugged in), turned on, and the eye pad heated up to the right temperature. The indictor light can turn from red to green on the charging base, indicating that the desired temperature has been reached in the eye pad. The eye pad can then be applied on a closed eye for, say, two to three minutes, then removed from the eye, and placed back in the well to reheat it for the second eye. Alternatively, the eye pad could remain on the eyelid during treatment.

The roller can then be removed from the charging well, the indicator light on the handle having turned from red to green to indicate that the roller cylinder is in the proper temperature range. The user can then hold the handle firmly by hand, while in front of a mirror, and place the roller cylinder at the base of the lower eyelid and gently press on the eyelid and roll up towards the lashes. This motion can be repeated two to three times at each section of the lower eyelid until the user has covered the whole eyelid. The roller can then be applied to the upper eyelid, repeating the same steps as on the lower eyelid, except with a downward motion from the top of the upper eyelid towards the lashes. (The lower and upper eyelids can be done in either order.) The process is then repeated for the second eye. The user can then wash away the extruded meibomian gland debris with the presoaked sweeping applicators and wash the face with lukewarm water.

Figure 8:
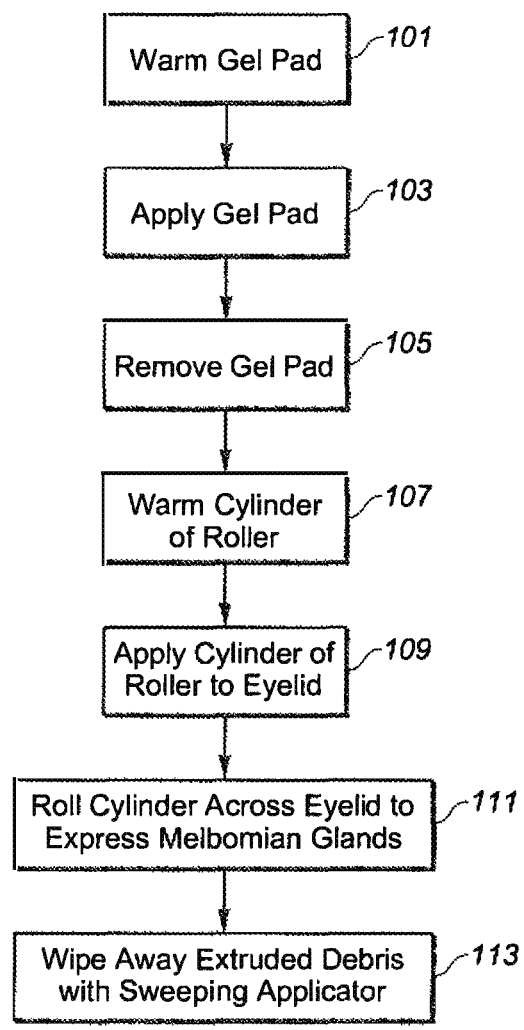
FIG. 8 is a flow to illustrate use of the meibomian gland roller.

FIG. 8 is a flowchart illustrating an example use of the meibomian gland roller. At 101, a gel eye pad is heated, applied to the user's eyelid at 103, and then removed at 105. At 109, the cylinder of the roller is used to apply pressure to the user's eyelid, having previously been heated at 107. The user can then roll the cylinder across the user's eyelid at 111 to express the meibomian glands of the eyelid. At 113, the extruded meibomian gland debris is washed away with the sweeping applicators.

In an alternate set of embodiments, the heated roller can interface with a smartphone or similar device for power, communication, or both. For example, a smartphone application might be used to control and/or monitor its use and the frequency of use. Additionally, in some embodiments the handle could be connected to the smartphone to receive power.

The apparatus and techniques described above allow for the long term, regular maintenance of meibomian gland function by users themselves. Under previous arrangements, maintenance would involve going to a professional eye care practice for a patient to go through expensive meibomian gland drainage procedures. In between these procedures, which can be expensive, patients would rely upon maintenance procedures that can lack ease of use and that are of uncertain effectivity. In contrast, the procedures presented here are designed for ease of usage and effectiveness, allowing for a regular maintenance of the glands for an effective treatment regime.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. In the foregoing specification, embodiments of the invention have been described with reference to numerous specific details that may vary from implementation to implementation. The sole and exclusive indicator of the scope of the invention, and what is intended by the applicants to be the scope of the invention, is the literal and equivalent scope of the set of claims that issue from this application, in the specific form in which such claims issue, including any subsequent correction. Further embodiments can be envisioned to one of ordinary skill in the art after reading this disclosure. In other embodiments, combinations or sub-combinations of the above-disclosed invention can be advantageously made. The example arrangements of components are shown for purposes of illustration and combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

What is claimed is:

1. An eye treatment system comprising:
a handle comprising:
   a power source; and
   control circuitry coupled to the power source;
an axle comprising a heating element;
a cylinder that is configured to rotate about the axle, wherein the cylinder includes a temperature sensor that is adjacent a surface of the cylinder for monitoring a temperature of the surface and that is spaced apart from the heating element;
one or more arms that couple a first end of the handle to the axle, wherein at least one of the one or more arms houses first wiring through which power is supplied from the power source to the heating element and houses second wiring connecting the temperature sensor to the control circuitry; and
a plurality of sweeping applicators comprising individually foil-wrapped double ended sweepers each with a presoaked gauze tip.

2. The eye treatment system of claim 1, further comprising a soft gel eye pad that is configured to be warmed and applied to an eyelid of a user.

3. The eye treatment system of claim 2, further comprising a charging well structure comprising a heating well configured to receive and heat the soft gel eye pad.

4. The eye treatment system of claim 3, wherein the charging well structure comprises a charging well configured to receive an end of the handle and charge the power source of the handle.

5. The eye treatment system of claim 3, wherein the charging well structure comprises an indicating light configured to indicate when both the cylinder is within a first temperature range and the soft gel eye pad is within a second temperature range.

6. The eye treatment system of claim 1, wherein the control circuitry is configured to regulate the temperature of the surface of the cylinder using the heating element.

7. The eye treatment system of claim 1, wherein the heating element is housed in the axle.

8. The eye treatment system of claim 1, wherein the heating element comprises a heating coil.

9. The eye treatment system of claim 1, wherein a width of the cylinder is in a 1-2 cm range and configured to be applied to an eyelid of a user.

10. The eye treatment system of claim 1, wherein the handle is connectable to a mobile device to receive power and/or be controlled by an application on the mobile device.

11. A method comprising:
warming a first surface of a first cylinder of a roller to a first temperature within a first temperature range, the roller comprising an axle and a handle, wherein the first cylinder is connected to a first end of the handle by at least one arm, and wherein the at least one arm houses first wiring through which power is supplied from a power source of the handle to a heating element and houses second wiring connecting a temperature sensor of the first cylinder to control circuitry;
applying pressure to a first eyelid of a first user by the first cylinder;
rolling the first cylinder that is warmed to the first temperature within the first temperature range across the first eyelid of the first user to express a first meibomian gland;
washing away extruded meibomian gland debris with one or more presoaked sweeping applicators;
replacing the first cylinder of the roller with a second cylinder; and
warming a second surface of the second cylinder and applying pressure to a second eyelid of a second user by the second cylinder.

12. The method of claim 11, further comprising warming a soft gel eye pad and applying the soft gel eye pad to the first user or the second user.

13. The method of claim 12, further comprising receiving and heating the soft gel eye pad in a charging well structure comprising a heating well.

14. The method of claim 13, further comprising receiving, by a charging well of the charging well structure, an end of the handle and charging the power source of the handle.

15. The method of claim 13, further comprising indicating, by an indicating light, when both the first cylinder is within the first temperature range and the soft gel eye pad is within a second temperature range.

16. The method of claim 11, further comprising regulating the temperature of the first surface of the first cylinder using the heating element.

17. The method of claim 11, wherein the heating element is housed in the axle.

18. The method of claim 11, wherein the axle comprises the heating element that comprises a heating coil.

19. The method of claim 11, wherein a width of the first cylinder is in a 1-2 cm range.

20. The method of claim 11, further comprising connecting the handle to a mobile device to receive power and/or be controlled by an application on the mobile device.

* * * * *